US007378512B2

(12) United States Patent
Rumenapf et al.

(10) Patent No.: US 7,378,512 B2
(45) Date of Patent: May 27, 2008

(54) PRODUCTION OF PROTEINS BY AUTOPROTEOLYTIC CLEAVAGE

(75) Inventors: Tillmann Rumenapf, Fernwald (DE); Heinz J Thiel, Giessen (DE); Jorg Windisch, Kramsach (AT); Franz Knauseder, Kirchbichl (AT)

(73) Assignee: Biochemie Gesellschaft m.b.H, Kundle (AT)

( * ) Notice: Subject to any disclaimer, the term of this patent is extended or adjusted under 35 U.S.C. 154(b) by 308 days.

(21) Appl. No.: 10/763,619

(22) Filed: Jan. 23, 2004

(65) Prior Publication Data

US 2004/0215008 A1 Oct. 28, 2004

Related U.S. Application Data

(63) Continuation of application No. 10/048,872, filed as application No. PCT/EP00/07642 on Aug. 7, 2000, now abandoned.

(30) Foreign Application Priority Data

Aug. 9, 1999 (AT) .................................... 1368/99

(51) Int. Cl.

| | |
|---|---|
| ***C12N 15/62*** | (2006.01) |
| ***C12N 15/57*** | (2006.01) |
| ***C12N 15/40*** | (2006.01) |
| ***C12N 15/70*** | (2006.01) |
| ***C12N 9/48*** | (2006.01) |

(52) U.S. Cl. .................... 536/23.4; 435/69.7; 435/212; 435/252.31; 435/320.1; 536/23.2

(58) Field of Classification Search ..................... None
See application file for complete search history.

(56) References Cited

U.S. PATENT DOCUMENTS

| | | | | |
|---|---|---|---|---|
| 5,149,783 A | | 9/1992 | Sommergruber et al. | |
| 6,077,694 A | * | 6/2000 | Medabalimi | 435/69.7 |
| 6,936,455 B1 | * | 8/2005 | Stempfer et al. | 435/212 |

FOREIGN PATENT DOCUMENTS

| | | |
|---|---|---|
| CA | 2301698 | 3/1999 |
| EP | 234888 | 9/1987 |
| EP | 321973 | 6/1989 |
| WO | WO 98/49326 | 11/1998 |
| WO | WO 99/10483 | 3/1999 |
| WO | WO 99/10503 | 3/1999 |

OTHER PUBLICATIONS

Thiel, H.-J., et al., 1992, "Proteins encoded in the 5'regiohn of the pestivirus genome—considerations concerning taxonomy", Veterinary Microbiology, vol. 33, pp. 213-219.*

Scaramozzino, N., et al., 2002, "Les proteases virales dans la famille des Flaviviridae" [The viral proteases in the Flavivirus family], Virologie, vol. 6, pp. 445-454.*

Hughes, A. L., 2004, Evolutionalry origin of the Hiv90 gene of Pestivirus, Infection, Genetics and Evolution, vol. 4, pp. 329-333.*

Collins-Racie et al., Bio-Technology, vol. 13, No. 9, 982-987 (1995).

Muyldermans et al., Virus Genes, vol. 13, No. 2, 135-142 (1996).

Ruemenapf et al., J. of Virology, vol. 72, No. 3, 2544-2547 (1998).

Stark et al., J. of Virology, vol. 67, No. 12, 7088-7095 (1993).

Varnavski et al., Virology, vol. 255, 366-375 (1999).

Wiskerchen M. et al., J. Virology 65, pp. 4508-4514 (1991).

E. F. Rossomando, Methods in Enzymology, vol. 182: Guide to Protein Purification, Academic Press Inc., pp. 309-392 (1990).

Studier, F.W., Methods in Enzymology 185, pp. 60-89 (1990).

Abstract of oral presentation No. 4 V2 at the Jahrestagung Gesellschaft für Virologie, Hamburg, 10.-13.03 (1997).

Poster Abstract No. 7P33 at the Jahrestagung Gesellschaft für Virologie, Regensburg, Mar. 2-5, 1998.

Poster Abstract No. P2-46 at the Fifth International Symposium on Positive Strand RNA Viruses, St. Petersburg, Florida, May 23-28, 1998.

* cited by examiner

*Primary Examiner*—Nashaat T. Nashed
*Assistant Examiner*—William W. Moore
(74) *Attorney, Agent, or Firm*—Mark I. Bowditch

(57) ABSTRACT

The present invention relates to a process for the production of a heterologous polypeptide with homogeneous N-terminus in a bacterial host cell, wherein the heterologous polypeptide is autoproteolytically cleaved from an expressed fusion protein which comprises a polypeptide with the autoproteolytic activity of an autoprotease $N^{pro}$ of a pestivirus and the heterologous polypeptide by the $N^{pro}$ autoproteolytic activity.

17 Claims, No Drawings

SEQUENCE LISTING

<160> NUMBER OF SEQ ID NOS: 12

<210> SEQ ID NO 1
<211> LENGTH: 168
<212> TYPE: PRT
<213> ORGANISM: Pestivirus sp.

<400> SEQUENCE: 1

```
Met Glu Leu Asn His Phe Glu Leu Leu Tyr Lys Thr Ser Lys Gln Lys
  1               5                  10                  15

Pro Val Gly Val Glu Glu Pro Val Tyr Asp Thr Ala Gly Arg Pro Leu
             20                  25                  30

Phe Gly Asn Pro Ser Glu Val His Pro Gln Ser Thr Leu Lys Leu Pro
         35                  40                  45

His Asp Arg Gly Arg Gly Asp Ile Arg Thr Thr Leu Arg Asp Leu Pro
     50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165
```

<210> SEQ ID NO 2
<211> LENGTH: 168
<212> TYPE: PRT
<213> ORGANISM: Artificial Sequence
<220> FEATURE:
<223> OTHER INFORMATION: Description of Artificial Sequence:
Oligo-histidine purification aid combined with
sequence of Pestivirus

<400> SEQUENCE: 2

```
Met Ala Ser His His His His His His His Pro Val Gly Val Glu Glu
  1               5                  10                  15

Pro Val Tyr Asp Thr Ala Gly Arg Pro Leu Phe Gly Asn Pro Ser Glu
             20                  25                  30

Val His Pro Gln Ser Thr Leu Lys Leu Pro His Asp Arg Gly Arg Gly
         35                  40                  45

Asp Ile Arg Thr Thr Leu Arg Asp Leu Pro Arg Lys Gly Asp Cys Arg
     50                  55                  60

Ser Gly Asn His Leu Gly Pro Val Ser Gly Ile Tyr Ile Lys Pro Gly
 65                  70                  75                  80

Pro Val Tyr Tyr Gln Asp Tyr Thr Gly Pro Val Tyr His Arg Ala Pro
                 85                  90                  95

Leu Glu Phe Phe Asp Glu Ala Gln Phe Cys Glu Val Thr Lys Arg Ile
            100                 105                 110

Gly Arg Val Thr Gly Ser Asp Gly Lys Leu Tyr His Ile Tyr Val Cys
```

-continued

```
        115                 120                 125

Val Asp Gly Cys Ile Leu Leu Lys Leu Ala Lys Arg Gly Thr Pro Arg
    130                 135                 140

Thr Leu Lys Trp Ile Arg Asn Phe Thr Asn Cys Pro Leu Trp Val Thr
145                 150                 155                 160

Ser Cys Ser Asp Asp Gly Ala Ser
                165


<210> SEQ ID NO 3
<211> LENGTH: 16
<212> TYPE: PRT
<213> ORGANISM: Pestivirus sp.

<400> SEQUENCE: 3

Met Glu Leu Asn His Phe Glu Leu Leu Tyr Lys Thr Ser Lys Gln Lys
  1               5                  10                  15


<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:
      Oligo-histidine purification aid

<400> SEQUENCE: 4

Met Ala Ser His His His His His His His
  1               5                  10


<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5

ataattacta gttgtgctcc agtacctcca ggtgaag                              37


<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

ataattggat cctcgagtta ttacatttgc cgaagagccc tcaggc                    46


<210> SEQ ID NO 7
<211> LENGTH: 593
<212> TYPE: DNA
<213> ORGANISM: Homo sapiens

<400> SEQUENCE: 7

ataattacta gttgtgctcc agtacctcca ggtgaagatt ctaaagatgt agccgcccca     60

cacagacagc cactcacctc ttcagaacga attgacaaac aaattcggta catcctcgac    120

ggcatctcag ccctgagaaa ggagacatgt aacaagagta acatgtgtga aagcagcaaa    180

gaggcactgg cagaaaacaa cctgaacctt ccaaagatgg ctgaaaaaga tggatgcttc    240

caatctggat tcaatgagga gacttgcctg gtaaaaatca tcactggtct tttggagttt    300
```

-continued

```
gaggtatacc tagagtacct ccagaacaga tttgagagta gtgaggaaca agccagagct    360

gtgcagatga gtacaaaagt cctgatccag ttcctgcaga aaaaggcaaa gaatctagat    420

gcaataacca cccctgaccc aaccacaaat gccagcctgc tgacgaagct gcaggcacag    480

aaccagtggc tgcaggacat gacaactcat ctcattctgc gcagctttaa ggagttcctg    540

cagtccagcc tgagggctct tcggcaaatg taataactcg aggatccaat tat           593


<210> SEQ ID NO 8
<211> LENGTH: 347
<212> TYPE: PRT
<213> ORGANISM: Artificial Sequence
<220> FEATURE:
<223> OTHER INFORMATION: Description of Artificial Sequence:
      Oligo-histidine purification aid combined with
      sequences of Pestivirus and Homo sapiens

<400> SEQUENCE: 8

Met Ala Ser His His His His His His His Pro Val Gly Val Glu Glu
  1               5                  10                  15

Pro Val Tyr Asp Thr Ala Gly Arg Pro Leu Phe Gly Asn Pro Ser Glu
             20                  25                  30

Val His Pro Gln Ser Thr Leu Lys Leu Pro His Asp Arg Gly Arg Gly
         35                  40                  45

Asp Ile Arg Thr Thr Leu Arg Asp Leu Pro Arg Lys Gly Asp Cys Arg
     50                  55                  60

Ser Gly Asn His Leu Gly Pro Val Ser Gly Ile Tyr Ile Lys Pro Gly
 65                  70                  75                  80

Pro Val Tyr Tyr Gln Asp Tyr Thr Gly Pro Val Tyr His Arg Ala Pro
                 85                  90                  95

Leu Glu Phe Phe Asp Glu Ala Gln Phe Cys Glu Val Thr Lys Arg Ile
            100                 105                 110

Gly Arg Val Thr Gly Ser Asp Gly Lys Leu Tyr His Ile Tyr Val Cys
        115                 120                 125

Val Asp Gly Cys Ile Leu Leu Lys Leu Ala Lys Arg Gly Thr Pro Arg
    130                 135                 140

Thr Leu Lys Trp Ile Arg Asn Phe Thr Asn Cys Pro Leu Trp Val Thr
145                 150                 155                 160

Ser Cys Ala Pro Val Pro Pro Gly Glu Asp Ser Lys Asp Val Ala Ala
                165                 170                 175

Pro His Arg Gln Pro Leu Thr Ser Ser Glu Arg Ile Asp Lys Gln Ile
            180                 185                 190

Arg Tyr Ile Leu Asp Gly Ile Ser Ala Leu Arg Lys Glu Thr Cys Asn
        195                 200                 205

Lys Ser Asn Met Cys Glu Ser Ser Lys Glu Ala Leu Ala Glu Asn Asn
    210                 215                 220

Leu Asn Leu Pro Lys Met Ala Glu Lys Asp Gly Cys Phe Gln Ser Gly
225                 230                 235                 240

Phe Asn Glu Glu Thr Cys Leu Val Lys Ile Ile Thr Gly Leu Leu Glu
                245                 250                 255

Phe Glu Val Tyr Leu Glu Tyr Leu Gln Asn Arg Phe Glu Ser Ser Glu
            260                 265                 270

Glu Gln Ala Arg Ala Val Gln Met Ser Thr Lys Val Leu Ile Gln Phe
        275                 280                 285

Leu Gln Lys Lys Ala Lys Asn Leu Asp Ala Ile Thr Thr Pro Asp Pro
    290                 295                 300
```

-continued

Thr Thr Asn Ala Ser Leu Leu Thr Lys Leu Gln Ala Gln Asn Gln Trp
305 310 315 320

Leu Gln Asp Met Thr Thr His Leu Ile Leu Arg Ser Phe Lys Glu Phe
325 330 335

Leu Gln Ser Ser Leu Arg Ala Leu Arg Gln Met
340 345

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Oligonucleotide

<400> SEQUENCE: 9
ataattacta gttgttgtga tctgcctcaa acccacagcc 40

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Oligonucleotide

<400> SEQUENCE: 10
ataattggat cctcgagtta ttattcctta cttcttaaac tttcttgcaa g 51

<210> SEQ ID NO 11
<211> LENGTH: 533
<212> TYPE: DNA
<213> ORGANISM: Homo sapiens

<400> SEQUENCE: 11
ataattacta gttgttgtga tctgcctcaa acccacagcc tgggtagcag gaggaccttg 60
atgctcctgg cacagatgag gagaatctct cttttctcct gcttgaagga cagacatgac 120
tttggatttc cccaggagga gtttggcaac cagttccaaa aggctgaaac catccctgtc 180
ctccatgaga tgatccagca gatcttcaat ctcttcagca caaaggactc atctgctgct 240
tgggatgaga ccctcctaga caaattctac actgaactct accagcagct gaatgacctg 300
gaagcctgtg tgatacaggg ggtgggggtg acagagactc ccctgatgaa ggaggactcc 360
attctggctg tgaggaaata cttccaaaga atcactctct atctgaaaga gaagaaatac 420
agcccttgtg cctgggaggt tgtcagagca gaaatcatga gatctttttc tttgtcaaca 480
aacttgcaag aaagtttaag aagtaaggaa taataactcg aggatccaat tat 533

<210> SEQ ID NO 12
<211> LENGTH: 327
<212> TYPE: PRT
<213> ORGANISM: Artificial Sequence
<220> FEATURE:
<223> OTHER INFORMATION: Description of Artificial Sequence: Oligo-histidine purification aid combined with sequences of Pestivirus and Homo sapiens

<400> SEQUENCE: 12

Met Ala Ser His His His His His His His Pro Val Gly Val Glu Glu
1 5 10 15

Pro Val Tyr Asp Thr Ala Gly Arg Pro Leu Phe Gly Asn Pro Ser Glu
20 25 30

-continued

```
Val His Pro Gln Ser Thr Leu Lys Leu Pro His Asp Arg Gly Arg Gly
         35                  40                  45

Asp Ile Arg Thr Thr Leu Arg Asp Leu Pro Arg Lys Gly Asp Cys Arg
    50                  55                  60

Ser Gly Asn His Leu Gly Pro Val Ser Gly Ile Tyr Ile Lys Pro Gly
65                  70                  75                  80

Pro Val Tyr Tyr Gln Asp Tyr Thr Gly Pro Val Tyr His Arg Ala Pro
                85                  90                  95

Leu Glu Phe Phe Asp Glu Ala Gln Phe Cys Glu Val Thr Lys Arg Ile
            100                 105                 110

Gly Arg Val Thr Gly Ser Asp Gly Lys Leu Tyr His Ile Tyr Val Cys
        115                 120                 125

Val Asp Gly Cys Ile Leu Leu Lys Leu Ala Lys Arg Gly Thr Pro Arg
    130                 135                 140

Thr Leu Lys Trp Ile Arg Asn Phe Thr Asn Cys Pro Leu Trp Val Thr
145                 150                 155                 160

Ser Cys Cys Asp Leu Pro Gln Thr His Ser Leu Gly Ser Arg Arg Thr
                165                 170                 175

Leu Met Leu Leu Ala Gln Met Arg Arg Ile Ser Leu Phe Ser Cys Leu
            180                 185                 190

Lys Asp Arg His Asp Phe Gly Phe Pro Gln Glu Glu Phe Gly Asn Gln
        195                 200                 205

Phe Gln Lys Ala Glu Thr Ile Pro Val Leu His Glu Met Ile Gln Gln
    210                 215                 220

Ile Phe Asn Leu Phe Ser Thr Lys Asp Ser Ser Ala Ala Trp Asp Glu
225                 230                 235                 240

Thr Leu Leu Asp Lys Phe Tyr Thr Glu Leu Tyr Gln Gln Leu Asn Asp
                245                 250                 255

Leu Glu Ala Cys Val Ile Gln Gly Val Gly Val Thr Glu Thr Pro Leu
            260                 265                 270

Met Lys Glu Asp Ser Ile Leu Ala Val Arg Lys Tyr Phe Gln Arg Ile
        275                 280                 285

Thr Leu Tyr Leu Lys Glu Lys Lys Tyr Ser Pro Cys Ala Trp Glu Val
    290                 295                 300

Val Arg Ala Glu Ile Met Arg Ser Phe Ser Leu Ser Thr Asn Leu Gln
305                 310                 315                 320

Glu Ser Leu Arg Ser Lys Glu
                325
```

PRODUCTION OF PROTEINS BY AUTOPROTEOLYTIC CLEAVAGE

This is a continuation of Ser. No. 10/048,872, abandoned, filed May 3, 2002, which is a 371 of PCT/EP00/07642, filed Aug. 7, 2000.

The present invention relates to a process for the production of a desired heterologous polypeptide with a clearly defined homogeneous N-terminus in a bacterial host cell, wherein the desired heterologous polypeptide is autoproteolytically cleaved from an initially expressed fusion protein which comprises a peptide with the autoproteolytic activity of an autoprotease $N^{pro}$ of a pestivirus and the heterologous polypeptide by the $N^{pro}$ autoproteolytic activity.

In the production of recombinant proteins in heterologous organisms such as the expression of human or other eukaryotic proteins in bacterial cells it is often difficult to obtain, a clearly defined N-terminus which is as nearly 100% homogeneous as possible. This applies in particular to recombinant pharmaceutical proteins whose amino acid sequence ought in many cases to be identical to the amino acid sequence naturally occurring in humans/animals.

On natural expression, for example in humans, many pharmaceutical proteins which are in use are transported into the extracellular space, and cleavage of the signal sequence present in the precursor protein for this purpose results in a clearly defined N-terminus. Such a homogeneous N-terminus is not always easy to produce, for example in bacterial cells, for several reasons.

Only in rare cases is export into the bacterial periplasm with the aid of a pro- or eukaryotic signal sequence suitable, because it is usually possible to accumulate only very small quantities of product here because of the low transport capacity of the bacterial export machinery.

However, the bacterial cytoplasm differs considerably from the extracellular space of eukaryotes. On the one hand, reducing conditions are present therein and, on the other hand, there is no mechanism for cleaving N-terminal leader sequences to form mature proteins. The synthesis of all cytoplasmic proteins starts with a methionine which is specified by the appropriate start codon (ATG=initiation of translation). This N-terminal methionine is retained in many proteins, while in others it is cleaved by the methionine aminopeptidase (MAP) present in the cytoplasm and intrinsic to the host. The efficiency of the cleavage depends essentially on two parameters: 1. the nature of the following amino acid, and 2. the location of the N-terminus in the three-dimensional structure of the protein. The N-terminal methionine is preferentially deleted when the following amino acid is serine, alanine, glycine, methionine or valine and when the N-terminus is exposed, i.e. not "hidden" inside the protein. On the other hand, if the following amino acid is a different one, in particular a charged one (glutamic acid, aspartic acid, lysine, arginine), or if the N-terminus is located inside the protein, in most cases cleavage of the N-terminal methionine does not occur (Knippers, Rolf (1995) Molekulare Genetik, 6th edition, *Georg Thieme Vedag*, Stuttgart, N.Y. ISBN 3-13-103916-7).

And even if an amino acid promoting the cleavage is present at position 2, the cleavage is rarely complete. It is usual for a not inconsiderable proportion (1-50%) to remain unaffected by the MAP.

In the early days of the production of recombinant pharmaceutical proteins in bacterial cells the procedure was simply to put a methionine-encoding ATG start codon in front of the open reading frame (ORF) for the mature (i.e.

without signal sequence or other N-terminal extension) protein. The expressed protein then had the sequence $H_2N$-Met-target protein. Only in a few cases was it possible to achieve complete cleavage of the N-terminal methionine by the MAP intrinsic to the host. Most of the proteins produced in this way therefore either are inhomogeneous in relation to their N-terminus (mixture of Met form and Met-free form) or they all have an additional foreign amino acid (Met) at the N-terminus (only Met form).

This inhomogeneity or deviation from the natural sequence is, however, unacceptable in many cases because these products frequently show different immunological (for example induction of antibody formation) and pharmacological (half-life, pharmacokinetics) properties. For these reasons, it is now necessary in most cases to produce a nature-identical product (homogeneous and without foreign amino adds at the N-terminus). In the case of cytoplasmic expression, the remedy here in most cases is to fuse a cleavage sequence (leader) for a specific endopeptidase (for example factor Xa, enterokinase, KEX endopeptidas s, IgA protease) or aminopeptidase (for example dipeptidyl aminopeptidas) to the N-terminus of the target protein. However, this makes an additional step, with expenditure of costs and materials, necessary during further working up, the so-called downstream processing, of the product.

There is thus a need for a process for producing a target protein in bacterial cells, the intention being that the target protein can be prepared with a uniform, desired N-terminus without elaborate additional in vitro steps (refolding, purification, protease cleavage, renewed purification etc.). Such a process using the viral autoprotease $N^{pro}$ from pestiviruses has been developed within the scope of the present invention.

Pestiviruses form a group of pathogens which cause serious economic losses in pigs and ruminants around the world. As the pathogen of a notifiable transmissible disease, the classical swine fever virus (CSFV) is particularly important. The losses caused by bovin viral diarrhoea virus (BVDV) are also considerable, especially through the regular occurrence of intrauterine infections of foetuses.

Pestiviruses are small enveloped viruses with a genome which acts directly as mRNA and is 12.3 kb in size and from which the viral gene products are transcribed in the cytoplasm. This takes place in the form of a single polyprotein which comprises about 4000 amino acids and which is broken down both by viral and by cellular proteases into about 12 mature proteins.

To date, two virus-encoded proteases have been identified in pestiviruses, the autoprotease $N^{pro}$ and the serine protease NS3. The N-terminal protease $N^{pro}$ is located at the N-terminus of the polyprotein and has an apparent molecular mass of 23 kd. It catalyses a cleavag which takes place between its own C-terminus (Cys168) and the N-terminus (Ser169) of nucleocapsid protein C(R. Stark et al., J. Virol. 67 (1993), 7088-7095). In addition, duplications of the $N^{pro}$ gene have been described in cytopathogenic BVDV viruses. In these there is a second copy of $N^{pro}$ at the N-terminus of the likewise duplicated NS3 protease. An autoproteolytic cleavage of the $N^{pro}$-NS3 protein is observed in this case too (R. Stark et al., see above).

$N^{pro}$ is an autoprotease with a length of 168 aa and an apparent $M_r$ of about 20,000 d (in vivo). It is the first protein in the polyprotein of pestiviruses (such as CSFV, BDV (border disease virus) or BVDV) and undergoes autoproteolytic cleavage from the following nucleocapsid protein C (M. Wiskerchen et al., J. Virol. 65 (1991), 4508-4514; Stark et al., J. Virol. 67 (1993), 7088-7095). This cleavage takes place after the last amino acid in the sequence of $N^{pro}$, Cys168.

It has now surprisingly been found within the scope of the present invention that the autoproteolytic function of an autoprotease $N^{pro}$ of a pestivirus is retained in bacterial expression systems, in particular on expression of heterologous proteins. The present invention thus relates to a process for the production of a desired heterologous polypeptide with a clearly defined homogeneous N-terminus in a bacterial host cell, wherein the desired heterologous polypeptide is cleaved from an initially expressed fusion protein which comprises a peptide with the autoproteolytic activity of an autoprotease $N^{pro}$ of a pestivirus and the heterologous polypeptide by the $N^{pro}$ autoproteolytic activity. The invention further relates to cloning means which are employed in the process according to the invention.

A polypeptide with the autoproteolytic activity of an autoprotease $N^{pro}$ of a pestivirus or a polypeptide with the autoproteolytic function of an autoprotease $N^{pro}$ of a pestivirus is, in particular, an autoprotease $N^{pro}$ of a pestivirus, or a derivative thereof with autoproteolytic activity.

Within the scope of the present invention, the term "heterologous polypeptide" means a polypeptide which is not naturally cleaved by an autoprotease $N^{pro}$ of a pestivirus from a naturally occurring fusion protein or polyprotein. Examples of heterologous polypeptides are industrial enzymes (process enzymes) or polypeptides with pharmaceutical, in particular human pharmaceutical, activity.

Examples of preferred polypeptides with human pharmaceutical activity are cytokines such as interleukins, for example lL-6, interferons such as leukocyte interferons, for example interferon α2B, growth factors, in particular haemopoletic or wound-healing growth factors, such as G-CSF, erythropoietin, or IGF, hormones such as human growth hormone (hGH), antibodies or vaccines.

In one aspect, the present invention thus relates to a nucleic add molecule which codes for a fusion protein where the fusion protein comprises a first polypeptide which has the autoproteolytic function of an autoprotease $N^{pro}$ of a pestivirus, and a second polypeptide which is connected to the first polypeptide at the C-terminus of the first polypeptide in a manner such that the second polypeptide is capable of being cleaved from the fusion protein by the autoproteolytic activity of the first polypeptide, and where the second polypeptide is a heterologous polypeptide.

The pestivirus for this purpose is preferably selected from the group of CSFV, BDV and BVDV, with CSFV being particularly preferred.

A preferred nucleic acid molecule according to the invention is one where the first polypeptide of the fusion protein comprises the following amino acid sequence of the autoprotease $N^{pro}$ of CSFV (see also EMBL database accession number X87939) (amino acids 1 to 168, reading from N-terminal to the C-terminal direction)

```
MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDEAQFCEVTKRIGRVTGSDGKLYHIYVCVDGCILLKLAKR

GTPRTLKWIRNFTNCPLWVTSC-(168), (SEQ ID NO: 1)
```

or the amino acid sequence of a derivative thereof with autoproteolytic activity.

Derivatives with autoproteolytic activity of an autoprotease $N^{pro}$ of a pestivirus are those autoproteases $N^{pro}$ produced by mutagenesis, in particular amino acid substitution, deletion, addition and/or amino acid insertion, as long as the required autoproteolytic activity, in particular for generating a desired protein with homogeneous N-terminus, is retained. Methods for generating such derivatives by mutagenesis are familiar to the skilled person. It is possible by such mutations to optimize the activity of the autoprotease $N^{pro}$, for example, in relation to different heterologous proteins to be cleaved. After production of a nucleic acid which codes for a fusion protein which, besides the desired heterologous protein, comprises an autoprotease $N^{pro}$ derivative which exhibits one or more mutations by comparison with a naturally occurring autoprotease $N^{pro}$, it is established whether the required function is present by determining the autoproteolytic activity in an expression system.

The autoproteolytic activity can, for example, intitially be detected by an in vitro system. For this purpose, the DNA construct is transcribed into RNA and translated into protein with the aid of an in vitro translation kit. In order to increase the sensitivity, the resulting protein is in some cases labelled by incorporation of a radioactive amino acid. The resulting $N^{pro}$-target protein fusion protein undergoes co- and/or post-translational autocatalytic cleavage, there being accurate cleavage of the N-terminal $N^{pro}$ portion by means of its autoproteolytic activity from the following target protein. The resulting cleavage products can easily be detected, and the mixture can be worked up immediately after completion of the in vitro translation reaction. The mixture is subsequently loaded onto a protein gel (for example Lāmmli SDS-PAGE) and subjected to electrophoresis. The gel is subseqeuntly stained with suitable dyes or autoradiographed. A Western blot with subsequent immunostaining is also possible. The efficiency of the cleavage of the fusion protein can be assessed on the basis of the intensity of the resulting protein bands.

In a further step, the nucleic acid fragment for the fusion protein can be cloned into a bacterial expression vector (if this has not already happened for the in vitro translation) and the latter can be transformed into an appropriate host (e.g. *E. coli*). The resulting expression strain expresses the fusion protein constitutively or after addition of an inducer. In the latter case it is necessary to cultivate further for one or more hours after addition of the inducer in order to achieve a sufficient titre of the product. The $N^{pro}$ autoprotease then cleaves itself co- or post-translationally from the expressed fusion protein so that the resulting cleavage fragments are the $N^{pro}$ autoprotease per se and the target protein with defined N-terminus. To evaluate the efficiency of this cleavage reaction, a sample is taken after the end of the cultivation or induction phase and analysed by SDS-PAGE as described above.

A preferred autoprotease $N^{pro}$ derivative of the described fusion protein has, for example, an N-terminal region in which one or more amino acids have been deleted or substituted in the region of amino acids 2 to 21 as long as the resulting derivative continues to exhibit th autoproteolytic function of the autoprotease $N^{pro}$ to the desired extent. In the context of the present invention, autoprotease $N^{pro}$ derivatives which are preferred in the fusion protein comprise, for example, the amino acid sequence of the autoprotease $N^{pro}$ of CSFV with a deletion of amino acids 2 to 16 or 2 to 21. It is also possible by amino acid substitution r addition to exchange or introduce amino acid sequences, for example in order to introduce an amino acid sequence which assists purification (see examples).

A particularly preferred nucleic acid molecule according to the present invention is one where the first polypeptide comprises the amino acid sequence Glu22 to Cys168 of th autoprotease $N^{pro}$ of CSFV or a derivative thereof with autoproteolytic activity, the first polypeptide furthermore having a Met as N-terminus, and the heterologous polypeptide being connected directly to the amino acid Cys168 of the autoprotease $N^{pro}$ of CSFV.

A likewise preferred nucleic acid molecule according to the present invention is one where the first polypeptide comprises the amino acid sequence Pro17 to Cys168 of the autoprotease $N^{pro}$ of CSFV or a derivative thereof with autoproteolytic activity, the first polypeptide furthermore having a Met as N-terminus, and the heterologous polypeptide being connected directly to the amino acid Cys168 of the autoprotease $N^{pro}$ of CSFV.

A nucleic acid molecule according to the invention is, in particular, in the form of a DNA molecule.

The present invention further relates to cloning elements, in particular expression vectors and host cells, which comprise a nucleic acid molecule according to the invention. Hence the present invention further relates to an expression vector which is compatible with a predefined bacterial host cell, comprising a nucleic acid molecule according to the invention and at least one expression control sequence. Expression control sequences are, in particular, promoters (such as lac, tac, T3, T7, trp, gac, vhb, lambda pL or phoA), ribosom binding sites (for example natural ribosome binding sites which belong to the abovementioned promoters, cro or synthetic ribosome binding sites), or transcription terminators (for example rmB T1T2 or bla). The above host cell is preferably a bacterial cell of the genus *Escherichia*, in particular *E. coli*. However, it is also possible to use other bacterial cells (see below). In a preferred embodiment, the expression vector according to the invention is a plasmid.

The present invention further relates to a bacterial host cell which comprises an expression vector according to the invention. Such a bacterial host cell can be selected, for example, from the group of the following microorganisms: Gram-negative bacteria such as *Escherichia* species, for example *E. coli*, or other Gram-negative bacteria, for example *Pseudomonas* sp., such as *Pseudomonas aeruginosa*, or *Caulobacter* sp., such as *Caulobacter crescentus*, or Gram-positive bacteria such as *Bacillus* sp., in particular *Bacillus subtlis*. *E. coli* is particularly preferred as host cell.

The present invention further relates to a process for the production of a desired heterologous polypeptide, comprising (i) cultivation of a bacterial host cell according to the present invention which comprises an expression vector according to the present invention which in turn comprises a nucleic acid molecule according to the present invention, wherein cultivation occurs under conditions which cause expression of the fusion protein and further autoproteolytic cleavage of the heterologous polypeptide from the fusion protein in the host cell by the autoproteolytic activity of the first polypeptide, and (ii) isolation of the cleaved heterologous polypeptide.

The process according to the invention is carried out in principle by initially cultivating the bacterial host cell, i.e. the expression strain, in accordance with microbiological practice known per se. The strain is generally brought up starting from a single colony on a nutrient medium, but it is also possible to employ cryopreserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). For the cultivation, a small-volume preculture of the host strain (inoculated with a single colony or with a cell suspension from a cryoculture) is grown, the temperature for this cultivation not generally being critical for the later expression result, so that it is possible routinely to operate at relatively high temperatures (for example 30° C. or 37° C.). The main culture is set up In a larger volume (for example 500 ml), where it is in particular necessary to ensure good aeration (large volume of flask compared with the volume of contents, high speed of rotation). Since it is intended that expression take place in soluble form, the main culture will in most cases also be carried out at a somewhat lower temperature (for example 22 or 28° C.). Both inducible systems (for example with trp, lac, tac or phoA promoter) and constitutive systems are suitable for producing soluble proteins. After the late logarithmic phase has been reached (usually at an optical density of 0.5 to 1.0 in shaken flasks), in inducible systems the inducer substance (for example indoleacrylic add, isopropyl β-D-thiogalactopyranoside=IPTG) is added and incubation is continued for 1 to 5 hours. The concentration of the inducer substance will in this case tend to be chosen at the lower limit in order to make careful expression possible. During this time, most of the $N^{pro}$-target protein fusion protein is formed, there being co- or post-translational cleavage of the $N^{pro}$ portion so that the two cleaved portions are present separately after the end of cultivation. The resulting cells can be harvested and processed further.

On a larger scale, the multistage system consists of a plurality of bioreactors (fermenters), it being preferred to employ defined nutrient media in this case in order to be able to improve the process engineering control of the process. In addition, it is possible greatly to increase biomass and product formation by metering in particular nutrients (fed batch). Otherwise, the process is analogous to the shaken flask. For example, a preliminary stage fermenter and a main stage fermenter are used, the cultivation temperature being chosen similar to that in the shaken flask. The preliminary stage fermenter is inoculated with a so-called inoculum which is generally grown from a single colony or a cryoculture in a shaken flask. Good aeration and a sufficient inducer concentration must also be ensured in the fermenter—and especially in the main stage thereof. The induction phase must, however, in some cases be made distinctly longer compared with the shaken flask. The resulting cells are once again delivered for further processing.

The heterologous target protein which has been cleaved from the fusion protein can then be isolated by protein purification methods known to the skilled person (see, for example, M. P. Deutscher, in: Methods in Enzymology: Guide to Protein Purification, Academic Press Inc., (1990), 309-392). A purification sequence generally comprises a cell disruption step, a clarification step (centrifugation or microfiltration) and various chromatographic steps, filtrations and precipitations.

The following examples serve to illustrate the present invention, without in any way limiting the scope thereof.

EXAMPLES

Example 1

Expression and in vivo Cleavage of an $N^{pro}$-C Fusion Protein in a Bacterial Host The plasmid NPC-pET is constructed for expression of an $N^{pro}$-C fusion protein in a bacterial host. The expression vector used is the vector pET11a (F.W. Studier et al., Methods. Enzymol. 185 (1990), 60-89). The natural structural gene (from the CSFV RNA genome) for the $N^{pro}$-C fusion protein is cloned into this expression vector. The structural gene for this fusion protein is provided by PCR amplification from a viral genome which has been transcribed into cDNA (and cloned into a vector). Moreover the first 16 amino acids of the natural $N^{Pro}$-sequence (SEQ ID NO: 3 MELNHFELLYKTSKQK) are replaced by a 10 amino acid-long oligo-histidine purification aid (SEQ ID NO: 4 MASHHHHHHH). The resulting construct is called NPC-pET. The sequence of the $N^{pro}$ portion and the autoproteolytic cleavage site of the $N^{pro}$-C fusion protein encoded on the NPC-pET has the following structure, with the cleavage site being located between the amino acids Cys168 and Ser(169):

```
MASHHHHHHHPVGVEEPVYDTAGRPLFGNPSEVHPQSTLKLPHD

RGRGDIRTTLRDLPRKGDCRSGNHLGPVSGIYIKPGPVYYQDYT

GPVYHRAPLEFFDEAQFCEVTKRIGRVTGSDGKLYHIYVCVDGC

ILLKLAKRGTPRTLKWIRNFTNCPLWVTSC(168)S(169)DDG

AS-(nucleocapsid protein C)(SEQ ID NO: 2)
```

In the sequence, proline 17 (position 2 of the fusion protein) from the natural $N^{pro}$ sequence is put in italics, and the start of the C sequence is printed in bold. The fusion protein has an approximate $M_r$ of 32 kd, with the $N^{pro}$ portion accounting for 18 kd and the C portion accounting for 14 kd after autoproteolytic cleavage.

In order to evaluate the significance of the first amino acid C-terminal of the cleavage site, the serine 169 which is naturally present there is replaced by the 19 other naturally occurring amino acids by targeted mutagenesis. The constructs produced thereby are called NPC-pET-Ala, NPC-pET-Gly etc. The expression strains are produced using these plasmids.

*Escherichia coli* BL21(DE3) is used as *Escherichia coli* host strain for expression of the $N^{pro}$-C fusion proteins. This strain has the following genotype:

*E. coli* B F dcm ompT hsdS($r_b^- m_b^-$) gal λ(DE3)

The strain is commercially available in the form of competent cells from Stratagene. It harbours a lysogenic lambda phage in the genome which comprises the gene for T7 RNA polymerase under the control of the lacUV5 promoter. Production of the 17 RNA polymerase and consequently also of the target protein can thus be induced by addition of isopropyl β-D-thiogalactopyranoside (IPTG). This two-stage system permits very high specific and absolute expression levels for many target proteins to be achieved.

The expression strains BL21(DE3)[MPC-pET], BL21 (DE3)[MPC-pET-Ala] etc. are produced by transforming the respective expression plasmid into BL21(DE3). The transformation takes place in accordance with the statements by the manufacturer of the competent cells (Stratagene or Novagen). The transformation mixture is plated out on Luria agar plates with 100 mg/l ampicillin. This transformation results in numerous clones in each case after incubation at 37° C. (overnight).

A medium-sized colony with distinct margins is picked and forms the basis for the appropriate expression strain. The clone is cultured and preserved in cryoampules at −80° C. (master cell bank MCB). The strain is streaked on Luria agar plates (with ampicillin) for daily use.

The particular strain is used for inoculating a preculture in a shaken flask from a single colony subcultured on an agar plate. An aliquot of the preculture is used to inoculate a main culture (10 to 200 ml in a shaken flask) and raised until the $OD_{600}$ is from 0.5 to 1.0. Production of the fusion protein is then induced with 1.0 mM IPTG (final concentration). The cultures are further cultivated for 2-4 h, an $OD_{600}$ of about 1.0 to 2.0 being reached. The cultivation temperature is 30° C.+/−2° C., and the medium used is LB medium+2 g/l glucos+100 mg/l ampicillin.

Samples are taken from the cultures before induction and at various times after induction and are centrifuged, and the pellets are boiled in denaturing sample buffer and analysed by SDS-PAGE and Coomassie staining or Western blot. The samples are taken under standardized conditions, and differences in the density of the cultures are compensated by the volume of sample loading buffer used for resuspension.

The bands appearing after induction are located at somewhat above 20 kd ($N^{pro}$) and at about 14 kd (C). The efficiency of cleavage of the fusion protein with each construct is estimated on the basis of the intensity of the bands in the Coomassie-stained gel and in the W stem blot. It is found from this that most amino acids are tolerated at the position immediately C-terminal of the cleavage site (i.e. at the N-terminus of the target protein), i.e. very efficient autoproteolytic cleavage takes place.

These data show that it is possible in principle to employ successfully the autoproteolytic activity of the autoprotease $N^{pro}$ for the specific cleavage of a recombinant fusion protein in a bacterial host cell.

Example 2

Expression and in-vivo Cleavage of a Fusion Protein of $N^{pro}$ and Human Interleukin 6 (hIL6) to Produce Homogeneous Mature hIL6

The plasmid NP6-pET is constructed for expression of the $N^{pro}$-hIL6 fusion protein. pET11a (F. W. Studier et al., Methods. Enzymol. 185 (1990), 60-89) is used as expression vector. Firstly a fusion protein consisting of $N^{pro}$ and the CSFV nucleocapsid protein is cloned into this expression vector (see Example 1). The structural gene for this fusion protein is provided by a PCR. This entails the first 16 aa of the natural $N^{pro}$ sequence (SEQ ID NO: 3 MELNHFELLYKTSKQK) being replaced by a 10 aa-long oligo-histidine purification aid (SEQ ID NO: 4 MASHHHHHHH).

An SpeI cleavage site is introduced into the resulting expression plasmid at the junction between $N^{Pro}$ and nucleocapsid protein by targeted mutagenesis. This makes it possible to delete the structural gene for the nucleocapsid protein from the vector by restrictions with SpeI at the 5' end (corresponding to the N-terminus of the protein) and XhoI at the 3' end (corresponding to the C-terminus of the protein). The corresponding linearized $N^{pro}$-pET11a vector is removed from the nucleocapsid gene fragment by preparative gel electrophoresis. It is then possible to introduce the hIL6 structural gene via the "sticky" SpeI and XhoI ends.

The following preparatory work is necessary for this. The structural gene is amplified with the aid of a high-precision PCR (for example Pwo system from Roche Biochemicals, procedure as stated by the manufacturer) from an hIL6 cDNA clone which can be produced from C10-MJ2 cells. The following oligonucleotides are employed for this purpose:

Oligonucleotide 1 ("N-terminal"):

```
5'-ATAATTACTA GTTGTGCTCC AGTACCTCCA GGTGAAG-3'
(SEQ ID NO: 5)
```

Oligonucleotide 2 ("C-terminal"):

```
5'-ATAATTGGAT CCTCGAGTTA TTACATTTGC CGAAGAGCCC
TCAGGC-3' (SEQ ID NO: 6)
```

An SpeI cleavage site is introduced at the 5' end, and an XhoI cleavage site is introduced at the 3' end via the oligonucleotides used. In addition, a double ochre stop codon (TAATAA) is introduced at the 3' end of the structural gene for efficient termination of translation. The SpeI cleavage site at the front end permits ligation in reading frame with the $N^{pro}$-pET11a vector described above. The XhoI cleavage site at the rear end makes directed cloning in possible.

The sequence of the PCR fragment (593 bp) with the structural gene for hIL6 is depicted below (read in the N-terminal to C-terminal direction). The restriction cleavage sites are underlined, and the first codon of hIL6 (Ala) and the stop codon are printed in bold:

ATAATTACTAGTTGTGCTCCAGTACCTCCAGGTGAAGATTCTAAAGATGT
AGCCGCCCCACACAGACAGCCACTCACCTCTTCAGAACGAATTGACAAAC
AAATTCGGTACATCCTCGACGGCATCTCAGCCCTGAGAAAGGAGACATGT
AACAAGAGTAACATGTGTGAAAGCAGCAAAGAGGCACTGGCAGAAAACAA
CCTGAACCTTCCAAAGATGGCTGAAAAAGATGGATGCTTCCAATCTGGAT
TCAATGAGGAGACTTGCCTGGTAAAAATCATCACTGGTCTTTTGGAGTTT
GAGGTATACCTAGAGTACCTCCAGAACAGATTTGAGAGTAGTGAGGAACA
AGCCAGAGCTGTGCAGATGAGTACAAAAGTCCTGATCCAGTTCCTGCAGA
AAAAGGCAAAGAATCTAGATGCAATAACCACCCCTGACCCAACCACAAAT
GCCAGCCTGCTGACGAAGCTGCAGGCACAGAACCAGTGGCTGCAGGACAT
GACAACTCATCTCATTCTGCGCAGCTTTAAGGAGTTCCTGCAGTCCAGCC
TGAGGGCTCTTCGGCAAATGTAATAACTCGAGGATCCAATTAT
(SEQ ID NO: 7)

The construct produced by the ligation with the $N^{pro}$-pET11a plasmid is called NP6-pET.

The sequence of the $N^{pro}$-hIL6 fusion protein (347 amino acids, of which 162 amino acids for the $N^{pro}$ portion and 185 amino acids for the hIL6 portion), encoded on NP6-pET is depicted below, with the hIL6 sequence being printed in bold:

MASHHHHHHPVGVEEPVYDTAGRPLFGNPSEVHPQSTLKLPHDRGRGDI
RTTLRDLPRKGDCRSGNHLGPVSGIYIKPGPVYYQDYTGPVYHRAPLEFF
DEAQFCEVTKRIGRVTGSDGKLYHIYVCVDGCILLKLAKRGTPRTLKWIR
NFTNCPLWVTSCAPVPPGEDSKDVAAPHRQPLTSSERIDKQIRYILDGIS
ALRKETCNKSNMCESSKEALAENNLNLPKMAEKDGCFQSGFNEETCLVKI
ITGLLEFEVYLEYLQNRFESSEEQARAVQMSTKVLIQFLQKKAKNLDAIT
TPDPTTNASLLTKLQAQNQWLQDMTTHLILRSFKEFLQSSLRALRQM
(SEQ ID NO: 8)

The fusion protein has an $M_r$ of 39,303.76 d in the reduced state, and after a possible cleavage the $N^{pro}$ portion (reduced) would have an $M_r$ of 18,338.34 d and the hIL6 portion (reduced) would have 20,983.63 d. $N^{pro}$ has six cysteines and hIL6 four. It is likely that these cysteines are for the most part in reduced form in the bacterial cytoplasm. During the subsequent processing there is presumably at least partial formation of disulphide bridges. It must be expected that the N-terminal methionine in the fusion protein (or in the $N^{pro}$ portion) is mostly cleaved by the methionine aminopeptidase (MAP) intrinsic to the host, which would reduce the $M_r$ by about 131 d in each case to 39,172.76 d (fusion protein) and 18,207.13 d ($N^{pro}$).

The *Escherichia coli* host strain for expressing the $N^{pro}$-hIL6 fusion protein is *Escherichia coil* BL21(DE3) (see Example 1).

The expression strain BL21(DE3)[MP6-pET] is produced by transforming the expression plasmid MP6-pET described above into BL21(DE3) as described in Example 1.

The strain BL21(DE3)[MP6-pET] is subcultured from a single colony on an agar plate, which is then used to inoculate a preculture in Luria Broth+100 mg/l ampicillin (200 ml in a 1 l baffle flask). The preculture is shaken at 250 rpm and 30° C. for 14 h and reaches an $OD_{600}$ of about 1.0 during this. Then 10 ml portions of preculture are used to inoculate the main cultures (330 ml of Luria Broth in each 1l baffle flask) (3% inoculum). The main cultures are run at 30° C. (250 rpm) until the $OD_{600}$ has increased to 0.8, and then production of the fusion protein is induced with 0.5 or 1.0 mM IPTG (final concentration). The cultures are cultivated further at 30° C. and 250 rpm for 3 h, the $OD_{600}$ reaching about 1.0 to 2.0.

The cultures are transferred into sterile 500 ml centrifuge bottles and centrifuged at 10,000 g for 30 min. The centrifugation supernatant is completely discarded and the pellets are frozen at −80° C. until processed further.

The appearance of new protein bands in the complete lysate can easily be detected by Coomassie staining after SDS-PAGE. Bands with apparent molecular masses of about 19 kd, 21 kd and 40 kd appear in the lysate of BL21(DE3) [MP6-pET]. Analyses of this expression using specific anti-hIL6 antibodies essentially confirm the result obtained after Coomassie staining.

To optimize the $N^{pro}$-hIL6 cleavage, inductions are carried out at various temperatures and IPTG concentrations and again analysed both in the stained gel and by a Western blot Almost complete cleavage of $N^{pro}$-IL6 is observed at a culture temperature of 22° C.

This experiment shows that heterologous proteins can also be fused to the C-terminus of $N^{pro}$ in a bacterial expression system, and very efficient cleavage takes place. A change in the N-terminal amino acid of the following protein (alanine in place of serine) has no adverse effects either. This system is accordingly suitable according to the invention for producing recombinant proteins with homogeneous authentic N-terminus, especially in a heterologous expression system such as a bacterial expression system, without further processing steps.

Example 3

Expression and in-vivo Cleavage of a Fusion Protein Composed of $N^{pro}$ and Human Interferon α2B (IFNα2B) to Produce Homogeneous Mature IFNα2B The way of cloning IFNα2B to produce the vector NPI-pET corresponds to the way described for hIL6 in Example 2. The structural gene is amplified by high-precision PCR (for example Pwo system from Roche Biochemicals, procedure as stated by the manufacturer). The template used is an IFNα2B-cDNA clone which can be produced from human leukocytes by standard methods known to the skilled person. An alternative possibility is also to carry out a complete synthesis of the gene. The sequence of the structural gene is obtainable in electronic form via the Genbank database under accession number V00548. The following oligonucleotides are employed for the amplification:

Oligonucleotide 1 ("N-terminal"):

```
5'-ATAATTACTA GTTGTTGTGA TCTGCCTCAA ACCCACAGCC-3'
(SEQ ID NO: 9)
```

Oligonucleotide 2 ("C-terminal"):

```
5'-ATAATTGGAT CCTCGAGTTA TTATTCCTTA CTTCTTAAAC
TTTCTTGCAA G-3' (SEQ ID NO: 10)
```

The sequence of the PCR fragment (533 bp) with the structural gene for IFNα2B is depicted below. The restriction cleavage sites are underlined, and the first codon of IFNα2B (Cys) and the stop codon are printed in bold:

ATAATTACTAGTTGTTGTGATCTGCCTCAAACCCACAGCCTGGGTAGCAG
GAGGACCTTGATGCTCCTGGCACAGATGAGGAGAATCTCTCTTTTCTCCT
GCTTGAAGGACAGACATGACTTTGGATTTCCCCAGGAGGAGTTTGGCAAC
CAGTTCCAAAAGGCTGAAACCATCCCTGTCCTCCATGAGATGATCCAGCA
GATCTTCAATCTCTTCAGCACAAAGGACTCATCTGCTGCTTGGGATGAGA
CCCTCCTAGACAAATTCTACACTGAACTCTACCAGCAGCTGAATGACCTG
GAAGCCTGTGTGATACAGGGGGTGGGGGTGACAGAGACTCCCCTGATGAA
GGAGGACTCCATTCTGGCTGTGAGGAAATACTTCCAAAGAATCACTCTCT
ATCTGAAAGAGAAGAAATACAGCCCTTGTGCCTGGGAGGTTGTCAGAGCA
GAAATCATGAGATCTTTTTCTTTGTCAACAAACTTGCAAGAAAGTTTAAG
AAGTAAGGAATAATAACTCGAGGATCCAATTAT
(SEQ ID NO: 11)

The construct produced by ligation to the $N^{pro}$-pET11a plasmid is called NPI-pET.

The sequence of the $N^{pro}$-IFNα2B fusion protein (327 aa, of which 162 $N^{pro}$ and 165 IFNα2B) encoded on NPI-pET is depicted below, with the IFNα2B sequence being printed in bold (depicted in the direction from the N-terminus to the C-terminus):

MASHHHHHHPVGVEEPVYDTAGRPLFGNPSEVHPQSTLKLPHDRGRGDI
RTTLRDLPRKGDCRSGNHLGPVSGIYIKPGPVYYQDYTGPVYHRAPLEFF
DEAQFCEVTKRIGRVTGSDGKLYHIYVCVDGCILLKLAKRGTPRTLKWIR
NFTNCPLWVTSCCDLPQTHSLGSRRTLMLLAQMRRISLFSCLKDRHDFGF
PQEEFGNQFQKAETIPVLHEMIQQIFNLFSTKDSSAAWDETLLDKFYTEL
YQQLNDLEACVIQGVGVTETPLMKEDSILAVRKYFQRITLYLKEKKYSPC
AWEVVRAEIMRSFSLSTNLQESLRSKE(SEQ ID NO: 12)

The fusion protein has an $M_r$ of 37,591.44 d in the reduced state, and after a possible cleavage the $N^{pro}$ portion (reduced) would have an $M_r$ of 18,338.34 d and the IFNα2B portion (reduced) would have 19,271.09 d. $N^{pro}$ has six cysteines and IFNα2B four. It is likely that these cysteines are for the most part in reduced form in the bacterial cytoplasm. During the subsequent processing there is presumably at least partial formation of disulphide bridges. It must be expected that the N-terminal methionine in the fusion protein (or in the $N^{pro}$ portion) is mostly cleaved by the methionine aminopeptidase (MAP) intrinsic to the host, which would reduce the $M_r$ by about 131 d in each case to 37,460.23 d (fusion protein) and 18,207.13 d ($N^{pro}$).

The *Escherichia coli* host strain for expressing the $N^{pro}$-IFNα2B fusion protein is *Escherichia coli* BL21(DE3) (see Example 1).

The expression strain BL21(DE3)[NPI-pET] is produced by transforming the expression plasmid NPI-pET described above into BL21(DE3) as described in Example 1.

The strain BL21 (DE3)[NPI-pET] is subcultured from a single colony on an agar plate, and this is used to inoculate a preculture in Luria broth+100 mg/l ampicillin (200 ml in a 1 l baffle flask). The preculture is shaken at 250 rpm and 30° C. for 14 h and reaches an $OD_{600}$ of about 1.0 during this 10 ml portions of preculture are then used to inoculate the main cultures (330 ml of Luria broth in each 1 l baffle flask) (3% inoculum). The main cultures are run at 30° C. (250 rpm) until the $OD_{600}$ has increased to 0.8, and then production of the fusion protein is induced with 0.5 or 1.0 mM IPTG (final concentration). The cultures are cultivated further at 30° C. and 250 rpm for 3 h, during which an $OD_{600}$ of about 1.0 to 2.0 is reached.

The cultures are transferred into sterile 500 ml centrifuge bottles and centrifuged at 10,000 g for 30 min. The centrifugation supernatant is completely discarded, and the pellets are frozen at −80° C. until processed further.

The appearance of new protein bands in the complete lysate can easily be detected by Coomassie staining after SBS-PAGE. Molecular masses of about 38 kd and about 19 kd appear in the lysate of BL21 (DE3)[MP6-pET]. The IFNα2B band cannot be separated from the NP band by SDS-PAGE.

Analyses of these samples using specific anti-IFNα2B antibodies confirm the presence of a cleaved IFNα2B band.

To optimize the $N^{pro}$-IFNα2B cleavage, inductions are carried out at various temperatures and IPTG concentrations in this case too, and again analysed both in the stained gel and by a Western blot. It is also found in this case that optimal cleavage takes place at reduced temperatures (22 to 30° C.).

What is claimed is:

1. A nucleic acid molecule coding for a fusion protein comprising a first polypeptide which is a pestivirus autoprotease $N^{pro}$ and a second polypeptide which is covalently bound to the first polypeptide at the C-terminus of the first polypeptide in a manner such that the second polypeptide is capable of being cleaved from the fusion protein by the autoproteolytic activity of the first polypeptide, and where the second polypeptide is a heterologous with respect to the first polypeptide wherein said C-terminus of said first polypeptide is a cysteine at a position corresponding to position 168 of SEQ ID NO:1.

2. A nucleic acid molecule according to claim 1, wherein the pestivirus is selected from the group consisting of classical swine fever virus, border disease virus, and bovine viral diarrhea virus.

3. A nucleic acid molecule according to claim 2, wherein the pestivirus is classical swine fever virus.

4. A nucleic acid molecule according to claim 3, wherein the first polypeptide comprises the following amino acid sequence:

```
MELNHFELLYKTSKQKPVGVEEPVYDTAGRPLFGNPSEVHPQSTLK
LPHDRGRGDIRTTLRDLPRKGDCRSGNHLGPVSGIYIKPGPVYYQDYTGP
VYHRAPLEFFDEAQFCEVTKRIGRVTGSDGKLYHIYVCVDGCILLKLAKR
GTPRTLKWIRNFTNCPLWVTSC-(168)(SEQ ID NO: 1).
```

5. A nucleic acid molecule according to claim 1, wherein the first polypeptide consists of the amino acid sequence of SEQ ID NO. 1 in which one or more of amino acids 2-21 have been deleted or substituted, and wherein the first polypeptide has a Met as N-terminus.

6. A nucleic acid molecule according to claim 5, wherein the first polypeptide consists of the amino acid sequence of SEQ ID NO: 1 in which amino acids 2-16 have been deleted.

7. A nucleic acid molecule of claim 6, wherein the first polypeptide consists of the amino acid sequence of SEQ ID NO: 1 in which amino acids 2-21 have been deleted.

8. A nucleic acid molecule of claim 5, wherein amino acids 2-16 are replaced by a polypeptide consisting of 10 histadines.

9. A nucleic acid molecule according to claim 1, wherein the first polypeptide consists of an amino acid sequence corresponding to the amino acid sequence Glu22 to Cysl68 of the autoprotease $N^{pro}$ of classical swine fever virus and wherein the first polypeptide additionally has a Met as N-terminus, wherein said positions are determined by correspondence to positions 22 and 168 of SEQ ID NO:1.

10. A nucleic acid molecule according to claim 1, wherein the first polypeptide comprises an amino acid sequence corresponding to the amino acid sequence Pro17 to Cys168 of the autoprotease $N^{pro}$ of classical swine fever virus herein the first polypeptide has a Met as N-terminus wherein said positions are determined by correspondence to positions 17 and 168 of SEQ ID NO:1.

11. A nucleic acid molecule according to claim 1, wherein the nucleic acid molecule is a DNA molecule.

12. A nucleic acid molecule coding for a fusion protein comprising a first nucleic acid sequence encoding a first polypeptide consisting of an amino acid sequence corresponding to Glu22 to Cys168 of SEQ ID NO. 1 and having a Met as the N-terminus, and a second nucleic acid sequence encoding a second polypeptide which is heterologous with respect to the first polypeptide and is directly covalently bound to the C-terminus of the first polypeptide in a manner such that the second polypeptide is capable of being cleaved from the fusion protein by the autoproteolytic activity of the first polypeptide.

13. An expression vector which is compatible with a predefined bacterial host cell, comprising a nucleic acid molecule according to claim 1, and at least one expression control sequence.

14. An expression vector according to claim 13, wherein the bacterial host cell is an E. coli cell.

15. An expression vector according to claim 13, wherein the expression vector is a plasmid.

16. A bacterial host cell comprising a vector according to claim 13.

17. A bacterial host cell according to claim 16, wherein the host cell is an E. coli cell.

* * * * *